(12) United States Patent
Lebedev

(10) Patent No.: US 7,589,241 B1
(45) Date of Patent: Sep. 15, 2009

(54) PROCESS FOR SEPARATING TERTIARY ALCOHOLS FROM SECONDARY ALCOHOLS FROM PINE OIL

(75) Inventor: Mikhail Y. Lebedev, Jacksonville, FL (US)

(73) Assignee: Millennium Specialty Chemicals, Inc., Houston, TX (US)

( * ) Notice: Subject to any disclaimer, the term of this patent is extended or adjusted under 35 U.S.C. 154(b) by 0 days.

(21) Appl. No.: 12/317,903

(22) Filed: Dec. 30, 2008

(51) Int. Cl.
*C07C 35/18* (2006.01)
(52) U.S. Cl. ........................................ 568/875; 568/868
(58) Field of Classification Search ................ 568/868, 568/875
See application file for complete search history.

(56) References Cited

U.S. PATENT DOCUMENTS

| 4,755,311 A | * | 7/1988 | Burjes et al. ................. 508/188 |
| 5,614,480 A | * | 3/1997 | Salomon et al. ............. 508/287 |
| 5,663,130 A | * | 9/1997 | Emert et al. ................. 508/506 |

* cited by examiner

*Primary Examiner*—Elvis O Price
(74) *Attorney, Agent, or Firm*—Jarrod N. Raphael

(57) ABSTRACT

A process for separating at least one tertiary alcohol from at least one secondary alcohol from pine oil, the process comprising:
reacting the pine oil comprising the at least one secondary alcohol and the at least one tertiary alcohol with at least one organic carbonate, and at least one base, wherein the secondary alcohol is esterified to produce at least one secondary ester; and
separating the tertiary alcohol from the secondary ester.

20 Claims, No Drawings

PROCESS FOR SEPARATING TERTIARY ALCOHOLS FROM SECONDARY ALCOHOLS FROM PINE OIL

FIELD OF INVENTION

The present inventive subject matter generally relates to a novel process for separating tertiary alcohols from secondary alcohols from pine oil.

BACKGROUND OF INVENTION

Pine oil, which can be derived as an essential oil from *Pinus sylvestris*, or alternatively, produced synthetically by acid-catalyzed reactions of terpenic hydrocarbons, alcohols, or diols in an aqueous media, comprises a variety of components, including a variety of terpenic alcohols. Of these terpenic alcohols, terpineol, which is a mixture of several tertiary alcohol isomers, including α-terpineol, β-terpineol, γ-terpineol, and 4-terpineol, has a pleasant floral odor similar to lilac and is widely used in high quality grades in consumer products in the fragrance and flavor industry. Along with terpineol, which has a boiling point of approximately 219° C. at normal pressure, several secondary terpenic alcohols, including fenchol and borneol which have boiling points of approximately 201° C. and 213° C. at normal pressure, respectively, are present in untreated pine oil, as well as other constituents, including various other terpenic alcohols, terpenic carbonyl compounds, terpene hydrocarbons, water, and other impurities. Separating terpineol from these and other constituents, as well as other low boiling impurities in pine oil, can be done relatively effectively and efficiently by employing traditional separation techniques given the differences in boiling points and solubilities.

However, although terpineol can be readily separated from water and other low boiling constituents in pine oil, terpineol cannot be readily separated from the secondary alcohols in pine oil, particularly fenchol and borneol. This is due to all three components having relatively similar boiling points, which does not allow the components to be separated easily by traditional separation techniques, particularly through distillation. Specifically, separating terpineol from borneol is an especially difficult task, since borneol co-distills with terpineol. Therefore, in order to sufficiently separate borneol from terpineol, multiple distillations or multiple other physical separations are usually required, which are not only time consuming, but are also energy inefficient, expensive to perform, can create a large amount of waste, and can denature the original terpineol in the pine oil, thus reducing the overall terpineol yield. Additionally, in order to produce high grade quality terpineol for acceptance by the consumer products industry, the terpineol has to satisfy strict requirements for purity, which is usually approximately 99% pure, as well as match industry odor standards. Accordingly, even relatively small amounts of impurities, including fenchol and borneol, can prevent a batch of terpineol from being considered high grade quality for use in consumer products.

Attempts have been made in the past to sufficiently separate the constituents of pine oil, including the processes outlined in U.S. Pat. No. 1,980,030, U.S. Pat. No. 2,050,671, and U.S. Pat. No. 1,800,862. In particular, the process outlined in U.S. Pat. No. 1,980,030 utilizes ortho-phosphoric acid to react with the terpenic or hydroaromatic alcohols in pine oil to produce the resultant phosphoric acid addition compounds. The resultant phosphoric acid addition compounds can then be separated from the pine oil through extraction, and then saponified back to the original alcohols. However, although the process of U.S. Pat. No. 1,980,030 generally separates the alcohols present in pine oil from the non-alcohols, the process does not allow one to separate the individual alcohols from one another, particularly tertiary alcohols from the other terpenic alcohols in pine oil.

With respect to U.S. Pat. No. 2,050,671, the process therein utilizes boric acid to separate both secondary and tertiary alcohols from pine oil. In particular, the process of U.S. Pat. No. 2,050,671 reacts boric acid with the terpenic alcohols in pine oil to produce the corresponding borates. The borates can then be separated from the pine oil by distillation, and then saponified back to the original alcohols. However, as with U.S. Pat. No. 1,980,030, although the process of U.S. Pat. No. 2,050,671 generally separates terpenic alcohols from non-alcohols present in pine oil, the process does not allow one to separate individual alcohols from one another, particularly tertiary alcohols from the other terpenic alcohols in pine oil.

As for U.S. Pat. No. 1,800,862, the process therein separates secondary alcohols from pine oil, including borneol and fenchol. In particular, the process of U.S. Pat. No. 1,800,862 begins with either preliminarily fractionating the pine oil to obtain fractions in which the secondary alcohols are concentrated, thereby removing most of the other constituents, including terpineol, or dehydrating the pine oil to remove the terpineol. After the secondary alcohols have been further concentrated, the secondary alcohols are then esterified with an organic acid and an acid catalyst, preferably hydrochloric acid, and recovered through distillation. However, although this process separates the secondary alcohols from pine oil, the terpineol is irrevocably destroyed by hydration.

Therefore, there remains a need in the art for a process to effectively and efficiently separate tertiary alcohols from the other constituents in pine oil. In particular, there remains a need in the art for a process to effectively and efficiently separate tertiary alcohols from secondary alcohols in pine oil.

SUMMARY OF INVENTION

The present inventive subject matter generally relates to a novel process for separating secondary alcohols and tertiary alcohols from pine oil. In this regard, an embodiment of the present inventive subject matter relates to a process for separating at least one tertiary alcohol from at least one secondary alcohol from pine oil, the process comprising:

reacting the pine oil comprising the at least one secondary alcohol and the at least one tertiary alcohol with at least one organic carbonate, and at least one base, wherein the secondary alcohol is esterified to produce at least one secondary ester; and separating the tertiary alcohol from the secondary ester.

Another embodiment of the present inventive subject matter relates to a process for separating terpineol from borneol and fenchol in pine oil, the process comprising:

treating the pine oil comprising the borneol, the fenchol, and the terpineol to substantially remove water present in the pine oil to produce a substantially anhydrous pine oil mixture;

substantially removing the fenchol from the substantially anhydrous pine oil mixture to produce a borneol and terpineol mixture;

reacting the borneol and terpineol mixture with at least one organic carbonate and at least one base, wherein the borneol is esterified to produce a borneol ester; and separating the terpineol from the borneol ester.

Additionally, in yet another embodiment, the present inventive subject matter relates to a process for producing fragrance-quality terpineol, the process comprising:

distilling pine oil comprising water, terpenes, fenchol, borneol, and terpineol to substantially remove the water, the terpenes, and the fenchol to produce a mixture comprising a majority of borneol and terpineol;

reacting the mixture comprising the majority of the borneol and the terpineol with at least one di-$C_1$-$C_8$-alkyl carbonate and at least one strong base, wherein the majority of the borneol is esterified to produce a borneol ester; and distilling the terpineol from the borneol ester, wherein the distilled terpineol comprises at least 95% by weight of the terpineol.

DETAILED DESCRIPTION OF INVENTION

Definitions

As used herein, the phrase "substantially remove", and like phrases, mean the component being removed is present at less than about 5% by weight, preferably less than about 1% by weight, and most preferably less than about 0.5% by weight after being removed.

As used herein, the phrase "substantially anhydrous", and like phrases, mean the water content is less than about 1% by weight, preferably less than about 0.5% by weight, and most preferably less than about 0.1% by weight after being removed.

Process:

The novel process of the present inventive subject matter allows for the separation of at least one tertiary alcohol from at least one secondary alcohol from pine oil. In a particular embodiment, the novel process of the present inventive subject matter relates to a process for separating at least one tertiary alcohol from at least one secondary alcohol from pine oil, the process comprising:

reacting the pine oil comprising the at least one secondary alcohol and the at least one tertiary alcohol with at least one organic carbonate, and at least one base, wherein the secondary alcohol is esterified to produce at least one secondary ester; and separating the tertiary alcohol from the secondary ester.

As discussed above, pine oil is composed of a variety of constituents, including secondary alcohols such as fenchol and borneol, as well as tertiary alcohols, such as terpineol, which can have high boiling points within approximately ±18° C. of each other. Therefore, separating the tertiary alcohols from the secondary alcohols can often be difficult, time consuming, expensive, and inefficient by conventional methods, including conventional chemical extraction and distillation methods. Accordingly, one of the benefits the present process can provide is a novel process in which tertiary alcohols, including terpineol, can be separated from pine oil, including separating the terpineol from the secondary alcohols in pine oil, which include fenchol, borneol, and mixtures thereof. In a preferred embodiment of the present process, the terpineol separated from the pine oil can include α-terpineol, γ-terpineol, and mixtures thereof.

In a particular embodiment, the process of the present subject matter separates at least one tertiary alcohol, including terpineol, from at least one secondary alcohol from pine oil, by reacting the secondary alcohol in the pine oil with at least one organic carbonate and at least one base to convert the secondary alcohol into a corresponding secondary ester. The tertiary alcohol can then be separated from the secondary ester in the pine oil by traditional separation methods, including, but not limited to, distillation with or without vacuum, and crystallization methods. In a particularly preferred embodiment, the secondary alcohol in the pine oil can be borneol, fenchol, and mixtures thereof, and the secondary ester can be borneol ester, fenchol ester, and mixtures thereof.

Furthermore, with previous techniques, in order to obtain tertiary alcohols with sufficient purity from pine oil, multiple traditional separation methods needed to be performed in order to separate the tertiary alcohols in pine oil, including terpineol, from the secondary alcohols in pine oil, including borneol, fenchol, and mixtures thereof. However, even after performing multiple traditional separations, many times the resultant tertiary alcohols produced are not of sufficient purity. Alternatively, preferred embodiments of the present process can produce at least 95% by weight, and preferably at least 99% by weight of at least one tertiary alcohol. Additionally, in other preferred embodiments, the process of the present subject matter can produce a tertiary alcohol comprising terpineol, wherein the terpineol comprises 50% by weight, and preferably 70% by weight of α-terpineol. In yet other embodiments of the present process, after the secondary alcohols are esterified into the corresponding secondary esters, the tertiary alcohol, including terpineol, can be separated from the secondary ester by traditional separation methods. In particular embodiments of the present process, after the secondary alcohols are esterified into the corresponding secondary esters, the tertiary alcohol, including terpineol, can be separated from the secondary ester in a single separation step or multiple separate steps, including but not limited to, a single distillation or multiple distillations.

Pine Oil:

In addition to the benefits discussed above, another benefit the present process can have is that any type of pine oil can be used, including "crude" (i.e., untreated) pine oil, or pre-treated pine oil, and the pine oil can be derived from natural sources such as *Pinus sylvestris*, or derived synthetically. Crude pine oil can generally have a starting tertiary alcohol content, including terpineol, ranging from about 20% to about 80% by weight, with the remaining content being composed of various impurities, including, but not limited to, water, other terpenic alcohols, including secondary terpenic alcohols such as fenchol and borneol, terpenic carbonyl compounds, pinenes, pinanols, and terpene hydrocarbons. In particular embodiments of the present process, crude pine oil which has not undergone any pretreatment can be used.

Alternatively, in other embodiments of the present process, pre-treated pine oil can be used, wherein the pre-treated pine oil can generally have a higher or lower tertiary alcohol content, including generally a higher or lower terpineol content than that of crude pine oil. In particular, the pine oil used in the present process can be treated in a variety of ways before use, including but not limited to, treating the pine oil before use by separating various components from the pine oil, including lower boiling impurities. Generally, components having a boiling point lower than approximately 200° C. at normal pressure, including water and low boiling impurities, can be separated before using the pine oil in the present process in a variety of ways, including separation processes utilizing differences in boiling points, including but not limited to distillation with or without a vacuum, differences in crystallization, differences in solubilites, and differences in polarity, which are well-known in the art. Examples of separation processes can be found in the *Kirk-Othmer Encyclopedia of Chemical Technology*, 5th edition, published by John Wiley & Sons.

Additionally, in particularly preferred embodiments of the present process, the pine oil can be pre-treated to substantially remove any number of various impurities, including, but not limited to, water, terpenic carbonyl compounds, pinenes, pinanols, and terpene hydrocarbons. Furthermore, in particular preferred embodiments of the present process, the pine oil can be treated to substantially remove at least the water present in the pine oil before being used. Additionally, in other particular preferred embodiments of the present process, the pine oil can be pre-treated to substantially remove the impurities previously mentioned, as well as various terpenic alcohols, including, but not limited to fenchol.

In embodiments in which the pine oil is treated to substantially remove the water present in the pine oil before the process is carried out, the amount of water substantially removed can be, but is not required to be, such that the resultant treated pine oil is substantially anhydrous. In yet another embodiment of the present process, the pine oil is treated to substantially remove at least the water and the fenchol present before the pine oil is used. Furthermore, in yet another embodiment of the present process, the pine oil is treated to substantially remove at least the water, the terpenes, and the fenchol present before the pine oil is used. Moreover, in particular preferred embodiments of the present process, crude pine oil can be pre-treated to remove a front cut of the pine oil with boiling temperatures up to about 201° C. at normal pressure, wherein the front cut is composed of various lower boiling impurities, including, but not limited to water, terpenic carbonyl compounds, pinenes, pinanols, terpene hydrocarbons, and fenchol. Accordingly, when a front cut with boiling temperatures up to about 201° C. at normal pressure is removed from the pine oil, the resultant mixture comprises a majority of terpineol and borneol. The resultant mixture comprising a majority of terpineol and borneol can then be reacted with at least one organic carbonate and at least one base to produce a mixture comprising terpineol and at least one borneol ester, with the terpineol then being separated from the borneol ester.

However, regardless of whether the pine oil used in the present process is crude pine oil or pre-treated pine oil, whether the pine oil is derived from natural sources or produced synthetically, as well as regardless to the amount of tertiary alcohol and terpineol content in the pine oil used, one of the benefits of the present process is that the process can separate the tertiary alcohols, including terpineol, from the secondary alcohols present in the pine oil.

Organic Carbonate:

The organic carbonates useful for the present process are those that can react with a secondary alcohol in the presence of a base to produce a corresponding secondary ester. Accordingly, various organic carbonates can be used with the present process, including using a single organic carbonate, or a mixture of various organic carbonates.

Generally, the organic carbonates useful for the present process can be at least one dialkyl carbonate. In preferred embodiments of the present process, the organic carbonate used can be at least one di-$C_1$-$C_8$-alkyl carbonate, wherein the alkyl groups can be the same or different. In particularly preferred embodiments of the present process, the organic carbonate can be at least one di-$C_1$-$C_6$-alkyl carbonate, wherein the alkyl groups can be the same or different.

Non-limiting examples of preferred organic carbonates include dimethyl carbonate, diethyl carbonate, ethylene carbonate, dipropyl carbonate, propylene carbonate, dibutyl carbonate, dipentyl carbonate, dihexyl carbonate, diheptyl carbonate, dioctyl carbonate, methyl ethyl carbonate, methyl heptyl carbonate, butyl heptyl carbonate, and mixtures thereof.

The amount of organic carbonate or carbonates used in the present process can be dependent upon the type of pine oil used. In particular, if crude pine oil is used, then generally a larger amount of at least one organic carbonate can be used. Alternatively, if pre-treated pine oil is used, especially pine oil which has been pre-treated to separate a front cut with boiling temperatures up to about 201° C. at normal pressure, then generally a lesser amount of at least one organic carbonate can be used. In general, the amount of the organic carbonate or carbonates used is dependent upon the concentration of secondary alcohols present in the pine oil to be subjected to the present process. Therefore, the higher the concentration of secondary alcohols in the pine oil to be treated, the greater the amount of at least one organic carbonate should be used. Contrastingly, the lower the concentration of the secondary alcohols in the pine oil to be treated, the lesser the amount of at least one organic carbonate should be used. Preferably, the molar concentration of organic carbonate or carbonates used to the molar concentration of secondary alcohols in the pine oil can be approximately 1:1.5 to 10:1. However, regardless of the concentration of secondary alcohols present in the pine oil used in the present process, at least one organic carbonate can be added in any amount, including but not limited to, an amount in excess.

In this regard, in preferred embodiments of the present process, at least one organic carbonate is added to pine oil with a base, wherein the organic carbonate esterifies at least one secondary alcohol in the pine oil to produce a secondary ester. In particularly preferred embodiments of the present process, at least one organic carbonate is added to pine oil, the pine oil comprising at least a mixture of terpineol and borneol, wherein the organic carbonate esterifies a majority of the borneol into a corresponding borneol ester. Additionally, in yet further particularly preferred embodiments of the present process, at least one organic carbonate is added to pine oil, the pine oil comprising at least a mixture of terpineol, borneol, and fenchol, wherein the organic carbonate esterifies a majority of the borneol and fenchol into at least one corresponding borneol ester and at least one fenchol ester.

Base:

The bases useful for the present process are those that can facilitate a reaction between a secondary alcohol and an organic carbonate. Therefore, various bases can be used with the present process, including the use of a single base, as well as a mixture of bases. Generally, the bases useful for the present process can be at least one strong base capable of establishing an equilibrium between reactants, with the base or bases comprising a pKa of the corresponding conjugate acid greater than about 5, more preferably greater than about 8. In preferred embodiments of the present process, the base or mixture of bases can comprise a pKa ranging from about 5 to about 40, and preferably from about 8 to about 25.

In particular embodiments of the present process, the base can be at least one strong inorganic base, at least one strong organic base, and mixtures thereof, including at least one metal hydroxide, metal carbonate, alkoxide, alkoxide salt, and mixtures thereof. Preferred metal hydroxides and metal carbonates include at least one alkali metal hydroxide, alkali metal carbonate, alkali earth metal hydroxide, and mixtures thereof. Particularly preferred metal hydroxides and metal carbonates include, but are not limited to, lithium hydroxide, sodium hydroxide, potassium hydroxide, cesium hydroxide, magnesium hydroxide, calcium hydroxide, sodium carbonate, potassium carbonate, cesium carbonate, and mixtures thereof.

Additionally, preferred alkoxides, and salts thereof, include at least one alkali metal alkoxide, alkali earth metal alkoxide, and mixtures thereof. Particularly preferred alkoxides include, but are not limited to, sodium methoxide, sodium ethoxide, sodium isopropoxide, potassium methoxide, potassium ethoxide, potassium isopropoxide, and mixtures thereof.

Furthermore, other inorganic bases can be used for the present process. Non-limiting examples of preferred inorganic bases also include sodium oxide, potassium oxide, calcium oxide, magnesium oxide, sodium hydride, sodium amide, metallic sodium, and mixtures thereof. In addition, ion-exchange resins such as Amberlite™ ion-exchange resins, including but not limited to Amberlite™ IRA-67, can also be used alone or in conjugation with other bases.

Moreover, other organic bases can be used for the present process. Non-limiting examples of additionally preferred organic bases include 1,8-diazabicyclo[5.4.0]undec-7-ene (DBU), 1,4-diazabicyclo[2.2.2]octane (DABCO), 4-(dimethylamino)pyridine (DMAP), and phosphazene bases, including, but not limited to, 2-tert-Butylimino-2-diethylamino-1,3-dimethylperhydro-1,3,2-diazaphosphorine, 2-tert-Butylimino-2-diethylamino-1,3-dimethylperhydro-1,3,2-diazaphosphorine, 2-tert-Butylimino-2-diethylamino-1,3-dimethylperhydro-1,3,2-diazaphosphorine, tert-Butylimino-tris(dimethylamino)phosphorane, Imino-tris(dimethylamino)phosphorane, 1,1,3,3,3-Pentakis(dimethylamino)-1$\lambda^5$,3$\lambda^5$-diphosphazene 1-oxide, phosphazene base $P_1$-t-Bu, phosphazene base $P_2$-t-Bu solution, phosphazene base $P_4$-t-Bu solution, phosphazene base $P_1$-t-Bu-tris(tetramethylene), phosphazene base $P_2$-Et, phosphazene base $P_1$-t-Oct, phosphazene base $P_4$-t-Oct solution, 1,8-bis(dimethylamino)naphthalene, and mixtures thereof.

The amount of base or bases used in the present process can be dependent upon the type of pine oil used. In particular, as with the amount of organic carbonate or carbonates used, if crude pine oil is used, then generally a larger amount of at least one base can be used. Additionally, since water may denature the base, the higher the water concentration is in the pine oil, the more base may be needed. Alternatively, if pre-treated pine oil is used, especially pine oil which has been pre-treated to separate a front cut with boiling temperatures up to about 201° C. at normal pressure, then generally a lesser amount of at least one base can be used. In general, the amount of base used can be dependent upon the concentration of water present in the pine oil, the relative strength and concentration of the base or bases used, and the concentration of secondary alcohols in the pine oil. Therefore, preferably, the molar concentration of the base or bases used to the molar concentration of secondary alcohols in the pine oil can be approximately about 1:0.5 to about 1:20, more preferably about 1:1 to about 1:10.

Alternatively, in additional embodiments of the present process, at least one base can be used in excess. However, if at least one base is used in excess, in preferred embodiments of the present process, the excess base is substantially neutralized before the tertiary alcohol is separated from the pine oil. Accordingly, if at least one base is used in excess, in a preferred embodiment of the present process, the excess base is neutralized such that the pine oil comprises a pH less than about 9, preferably less than about 8, and most preferably the pine oil comprises a pH ranging from about 4 to about 8.

EXAMPLES

The following examples are illustrative of preferred compositions, and are not intended to be limitations thereon. All product composition percentages are based on totals equal to 100% by gas chromatography analysis, and yield percentages are based on totals equal to 100% by weight, unless otherwise specified.

Test Methods:

Purity and composition percentages were determined using gas chromatography without a solvent on a 30-meter capillary column with a SPB-1 stationary phase on an Agilent Technologies 6890N GC.

Odor evaluations were performed by a panel of trained professionals comparing the odor profile and quality of compositions obtained against the odor and quality industry standard for terpineol.

Example 1

Crude pine oil is vacuum stripped to remove water, light hydrocarbons, and fenchol to give pre-treated pine oil (1000 g by GC: terpineol: 96.1%; fenchol: 0.15%; borneol: 2.73%). The pre-treated pine oil is mixed with dimethyl carbonate (150.0 g) and sodium hydroxide (40 g). The resulting mixture is stirred for 16 h at 130° C., 760 mm Hg to remove methanol. The reaction mixture is then distilled under vacuum at 20 mm Hg with a reflux ratio of 40:6 to give 565 g of material. The material (565 g) contains terpineol: 99.26%; fenchol: 0%; borneol: 0.59%. The blend passes an odor test when compared with an industry standard. Yield of in-spec α-terpineol: 56.5%.

Example 2

Crude pine oil is vacuum stripped to remove water, light hydrocarbons, and fenchol to give pre-treated pine oil (1038.1 g by GC; terpineol: 94.86%; fenchol: 0.02%; borneol: 1.42%). The pre-treated pine oil is mixed with diethyl carbonate (34.5 g) and sodium hydroxide (2.25 g of 85%). The resulting mixture is reacted under vacuum for 16 h at 125° C., 120 mm Hg. GC analysis of the reaction mixture shows the terpineol/borneol ratio has increased from 66.8 to 93.3. An additional amount of diethyl carbonate (34 g) is added and the reaction is continued for 7 h. GC analysis of the reaction mixture shows the terpineol/borneol ratio has increased to 267. The reaction mixture is then distilled under vacuum at 20 mm Hg with a reflux ratio of 40:8 to give ten cuts of 68 g residue. A first blend of cuts 4-10 (668.3 g) contains terpineol: 99.33%; fenchol: 0%; borneol: 0.25%. The first blend passes an odor test when compared with an industry standard.

Two additional blends, cuts 3-10 (763 g) and cuts 2-10 (858.7 g), do not pass the odor test. The odor of the two additional blends can be upgraded to passing using a fast re-distillation. A fast re-distillation is carried out under vacuum at 20 mm Hg and at 120° C.-130° C., with a reflux ratio of 40.8.

Example 3

Crude pine oil is vacuum stripped to remove water, light hydrocarbons, and fenchol to give pre-treated pine oil (1061 g by GC; terpineol: 94.75%; fenchol: 0.02%; borneol: 2.52%). The pre-treated pine oil is mixed with diethyl carbonate (82 g) and cesium carbonate (14.1 g). The resulting mixture is reacted under vacuum for 4 h at 125° C., with the pressure starting at 200 mm Hg and then reduced to 100 mm Hg. GC analysis of the reaction mixture shows the terpineol/borneol ratio has increased from 37.6 to 141. The reaction mixture is then distilled under vacuum at 20 mm Hg with a reflux ratio of 40:8 to give ten cuts of residue. A blend of cuts 4-10 (692.7 g) contains terpineol: 99.01%; fenchol: 0%; borneol: 0.26%. GC analysis of the blend shows the terpineol/borneol ratio is 381, but does not pass the odor test. The odor of this blend can be upgraded to passing using a fast re-distillation carried out under vacuum at 20 mm Hg and at 120° C.-130° C., with a reflux ratio of 40.8.

Example 4

Crude pine oil is vacuum stripped to remove water, light hydrocarbons, and fenchol to give pre-treated pine oil (1090.0 g by GC: terpineol: 97.6%; fenchol: 0.02%; borneol: 1.07%). The pre-treated pine oil is mixed with diethyl carbonate (26.6 g) and sodium ethoxide (13.1 g of 21% solution in ethanol). The resulting mixture is heated for 1 h at 90° C., 90 mm Hg. The reaction mixture is then distilled under vacuum at 20 mm Hg with a reflux ratio of 40:8 to give 960.5 g of material. The material (960.5 g) contains terpineol: 98.06%; fenchol: 0%; borneol: 0.33%; limonene: 0.6%. In order to reduce the amount of limonene, the material is distilled under vacuum at 21 mm Hg with a reflux ratio of 40:8 to give 793 g of re-distilled material. The material (793 g) contains terpineol: 99.3%; fenchol: 0%; borneol: 0.24%; limonene: 0.01%. Yield of in-spec α-terpineol: 72.8%.

Comparative Example 1

Crude Pine Oil Distillation without Organic Carbonate and Base

Crude pine oil (3865 g; GC: terpineol: 63.9%; fenchol: 8.06%; borneol: 2.34%) is distilled on 4' column at 10-20 mm Hg with a split ratio (R:R) of 40:8, corresponding to a take-off rate of 80.5 g/hr, to give 17 cuts. A blend of cuts 14-17 cuts (850 g) has a satisfactory GC analysis (terpineol: 99.1%; fenchol: 0%; borneol: 0.73%), but the yield is too low (22 wt. %). Moreover, its odor does not match that of the industry standard. This example shows that a single distillation of crude pine oil is inefficient for producing high-quality terpineol.

Comparative Example 2

Crude Pine Oil Distillation without Organic Carbonate and Base

Crude pine oil (1697.2 g; GC: terpineol: 62.1%; fenchol: 7.85%; borneol: 2.4%) is distilled on 4' column at 10-20 mm Hg with a split ratio (R:R) of 40:6, corresponding to a take-off rate of 57.2 g/hr, to give 17 cuts. A blend of cuts 12-17 cuts (550.2 g) has a satisfactory GC analysis (terpineol: 99.14%; fenchol: 0%; borneol: 0.68%), but even with the slower take-off rate, the yield is too low (32.4 wt. %). Moreover, its odor does not match that of the industry standard. This example shows that even a slower and longer single distillation of crude pine oil is inefficient for producing high-quality terpineol.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

I claim:

1. A process for separating at least one tertiary alcohol from at least one secondary alcohol from pine oil, the process comprising:
   reacting the pine oil comprising the at least one secondary alcohol and the at least one tertiary alcohol with at least one organic carbonate, and at least one base, wherein the secondary alcohol is esterified to produce at least one secondary ester; and
   separating the tertiary alcohol from the secondary ester.

2. The process of claim 1, wherein the pine oil further comprises water, and before the pine oil is reacted with the organic carbonate and the base, the pine oil is treated to substantially remove the water.

3. The process of claim 1, wherein the secondary alcohol is borneol, fenchol, or mixtures thereof.

4. The process of claim 1, wherein the secondary ester is borneol ester, fenchol ester, or mixtures thereof.

5. The process of claim 1, wherein the tertiary alcohol is terpineol.

6. The process of claim 1, wherein the tertiary alcohol is α-terpineol, γ-terpineol, or mixtures thereof.

7. The process of claim 1, wherein the organic carbonate is a dialkyl carbonate.

8. The process of claim 1, wherein the organic carbonate is a di-$C_1$-$C_8$-alkyl carbonate.

9. The process of claim 1, wherein the base is strong base.

10. The process of claim 1, wherein the base is a metal hydroxide, a metal carbonate, an alkoxide, an alkoxide salt, or mixtures thereof.

11. The process of claim 10, wherein the metal hydroxide is an alkali metal hydroxide, alkali earth metal hydroxide, or mixtures thereof.

12. The process of claim 1, wherein the base is selected from lithium hydroxide, sodium hydroxide, potassium hydroxide, cesium hydroxide, magnesium hydroxide, calcium hydroxide, sodium carbonate, potassium carbonate, cesium carbonate, sodium methoxide, sodium ethoxide, sodium isopropoxide, potassium methoxide, potassium ethoxide, potassium isopropoxide, 1,8-diazabicyclo[5.4.0]undec-7-ene (DBU), 1,4-diazabicyclo[2.2.2]octane (DABCO), 4-(dimethylamino)pyridine (DMAP), phosphazene bases, and mixtures thereof.

13. The process of claim 1, wherein the tertiary alcohol is separated from the secondary ester by distillation.

14. The process of claim 1, wherein the process produces at least 95% by weight of at least one tertiary alcohol.

15. The process of claim 1, wherein the process produces at least 99% by weight of at least one tertiary alcohol.

16. A process for separating terpineol from borneol and fenchol in pine oil, the process comprising:
   treating the pine oil comprising the borneol, the fenchol, and the terpineol to substantially remove water present in the pine oil to produce a substantially anhydrous pine oil mixture;
   substantially removing the fenchol from the substantially anhydrous pine oil mixture to produce a borneol and terpineol mixture;
   reacting the borneol and terpineol mixture with at least one organic carbonate and at least one base, wherein the borneol is esterified to produce a borneol ester; and
   separating the terpineol from the borneol ester.

17. A process for producing fragrance-quality terpineol, the process comprising:
  distilling pine oil comprising water, terpenes, fenchol, borneol, and terpineol to substantially remove the water, the terpenes, and the fenchol to produce a mixture comprising a majority of borneol and terpineol;
  reacting the mixture comprising the majority of the borneol and the terpineol with at least one di-$C_1$-$C_8$-alkyl carbonate and at least one strong base, wherein the majority of the borneol is esterified to produce a borneol ester; and
  distilling the terpineol from the borneol ester, wherein the distilled terpineol comprises at least 95% by weight of the terpineol.

18. The process of claim 17, wherein the distilled terpineol comprises at least 99% by weight of the terpineol.

19. The process of claim 17, wherein the distilled terpineol comprises at least 50% by weight of α-terpineol.

20. The process of claim 17, wherein the distilled terpineol comprises at least 70% by weight of α-terpineol.

* * * * *